US009730640B2

(12) United States Patent
Diab et al.

(10) Patent No.: US 9,730,640 B2
(45) Date of Patent: *Aug. 15, 2017

(54) PULSE OXIMETER PROBE-OFF DETECTOR

(71) Applicant: Masimo Corporation, Irvine, CA (US)

(72) Inventors: Mohamed K. Diab, Ladera Ranch, CA (US); Ammar Al-Ali, San Juan Capistrano, CA (US)

(73) Assignee: MASIMO CORPORATION, Irvine, CA (US)

( * ) Notice: Subject to any disclaimer, the term of this patent is extended or adjusted under 35 U.S.C. 154(b) by 165 days.

This patent is subject to a terminal disclaimer.

(21) Appl. No.: 14/023,153

(22) Filed: Sep. 10, 2013

(65) Prior Publication Data

US 2014/0100434 A1 Apr. 10, 2014

Related U.S. Application Data

(63) Continuation of application No. 12/345,537, filed on Dec. 29, 2008, now Pat. No. 8,532,728, which is a
(Continued)

(51) Int. Cl.
*A61B 5/1455* (2006.01)
*A61B 5/00* (2006.01)

(52) U.S. Cl.
CPC ........ *A61B 5/7221* (2013.01); *A61B 5/14551* (2013.01); *A61B 5/6843* (2013.01); *A61B 2560/0276* (2013.01)

(58) Field of Classification Search
CPC .............. A61B 5/1455; A61B 5/14551; A61B 5/14552; A61B 5/14532; A61B 5/0059;
(Continued)

(56) References Cited

U.S. PATENT DOCUMENTS 4,295,475 A 10/1981 Torzala
4,399,824 A 8/1983 Davidson
(Continued)

FOREIGN PATENT DOCUMENTS

DE 197 28 902 A1 7/1997
EP 0 182 197 A2 11/1985
(Continued)

OTHER PUBLICATIONS

PCT International Search Report, App. No. PCT/US00/08005, Date of Actual Completion of Search: Aug. 2, 2000, 2 pages.
(Continued)

*Primary Examiner* — Eric Winakur
*Assistant Examiner* — Chu Chuan (JJ) Liu
(74) *Attorney, Agent, or Firm* — Knobbe, Martens, Olson & Bear, LLP

(57) ABSTRACT

A processor provides signal quality based limits to a signal strength operating region of a pulse oximeter. These limits are superimposed on the typical gain dependent signal strength limits. If a sensor signal appears physiologically generated, the pulse oximeter is allowed to operate with minimal signal strength, maximizing low perfusion performance. If a sensor signal is potentially due to a signal induced by a dislodged sensor, signal strength requirements are raised. Thus, signal quality limitations enhance probe off detection without significantly impacting low perfusion performance. One signal quality measure used is pulse rate density, which defines the percentage of time physiologically acceptable pulses are occurring. If the detected signal contains a significant percentage of unacceptable pulses, the minimum required signal strength is raised proportionately. Another signal quality measure used in conjunction with pulse rate density is energy ratio, computed as the percent-
(Continued)

age of total energy contained in the pulse rate fundamental and associated harmonics.

23 Claims, 7 Drawing Sheets

Related U.S. Application Data continuation of application No. 10/721,607, filed on Nov. 25, 2003, now Pat. No. 7,471,969, which is a continuation of application No. 10/027,574, filed on Dec. 19, 2001, now Pat. No. 6,654,624, which is a continuation of application No. 09/531,820, filed on Mar. 21, 2000, now Pat. No. 6,360,114.

(60) Provisional application No. 60/126,148, filed on Mar. 25, 1999.

(58) Field of Classification Search
CPC ....... A61B 5/02; A61B 5/024; A61B 5/02416; A61B 5/0245; A61B 5/02455; A61B 5/04; A61B 5/04012; A61B 5/04015; A61B 5/0402; A61B 5/1495
USPC ....... 600/301, 322, 323, 330, 331, 336, 340, 600/345, 485, 509, 514, 519, 310, 502; 356/41
See application file for complete search history.

(56) References Cited

U.S. PATENT DOCUMENTS

| | | |
|---|---|---|
| 4,603,700 A | 8/1986 | Nichols et al. |
| 4,790,326 A * | 12/1988 | Mather ............... A61B 5/024 600/502 |
| 4,800,495 A * | 1/1989 | Smith ............... A61B 5/14551 600/323 |
| 4,955,379 A * | 9/1990 | Hall ............... A61B 5/14551 600/336 |
| 4,960,128 A | 10/1990 | Gordon et al. |
| 4,964,408 A | 10/1990 | Hink et al. |
| 5,041,187 A | 8/1991 | Hink et al. |
| 5,058,588 A * | 10/1991 | Kaestle ............... 600/323 |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| 5,348,005 A * | 9/1994 | Merrick et al. ............... 600/330 |
| 5,368,041 A | 11/1994 | Shambroom |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,846,190 A | 12/1998 | Woehrle |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |

(56) References Cited

U.S. PATENT DOCUMENTS

| | | |
|---|---|---|
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |

(56) References Cited

U.S. PATENT DOCUMENTS

| | | |
|---|---|---|
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |

(56) References Cited

U.S. PATENT DOCUMENTS

| | | |
|---|---|---|
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |

FOREIGN PATENT DOCUMENTS

| | | |
|---|---|---|
| EP | 0 315 040 A1 | 10/1988 |
| GB | 2 061 496 A | 10/1980 |
| JP | 09-108203 | 4/1997 |

OTHER PUBLICATIONS

PCT International Search Report, App. No. PCT/US00/16584, Date of Actual Completion of Search: Sep. 1, 2000, 4 pages.
Supplementary European Search Report, App. No. EP 00 91 6663, Date of Actual Completion of Search: Mar. 24, 2003, 2 pages.
Notice of Reasons for Rejection (Office Action) from International Application No. 2000-606119, Dec. 3, 2009 in 5 pages.
Extended European Search Report, App. No. EP 10 18 1436, Date of Actual Completion of Search: Nov. 26, 2010, 2 pages.

* cited by examiner

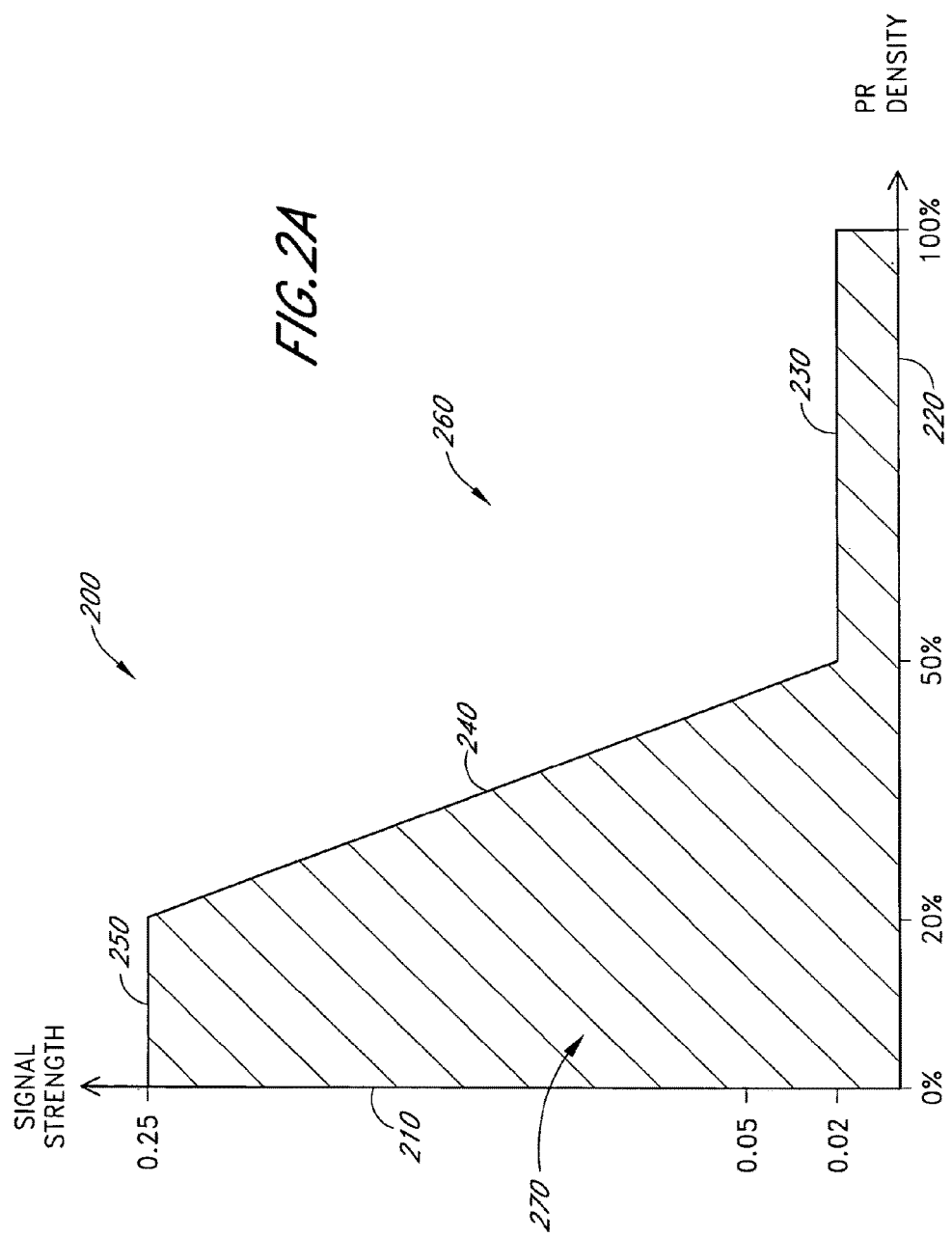

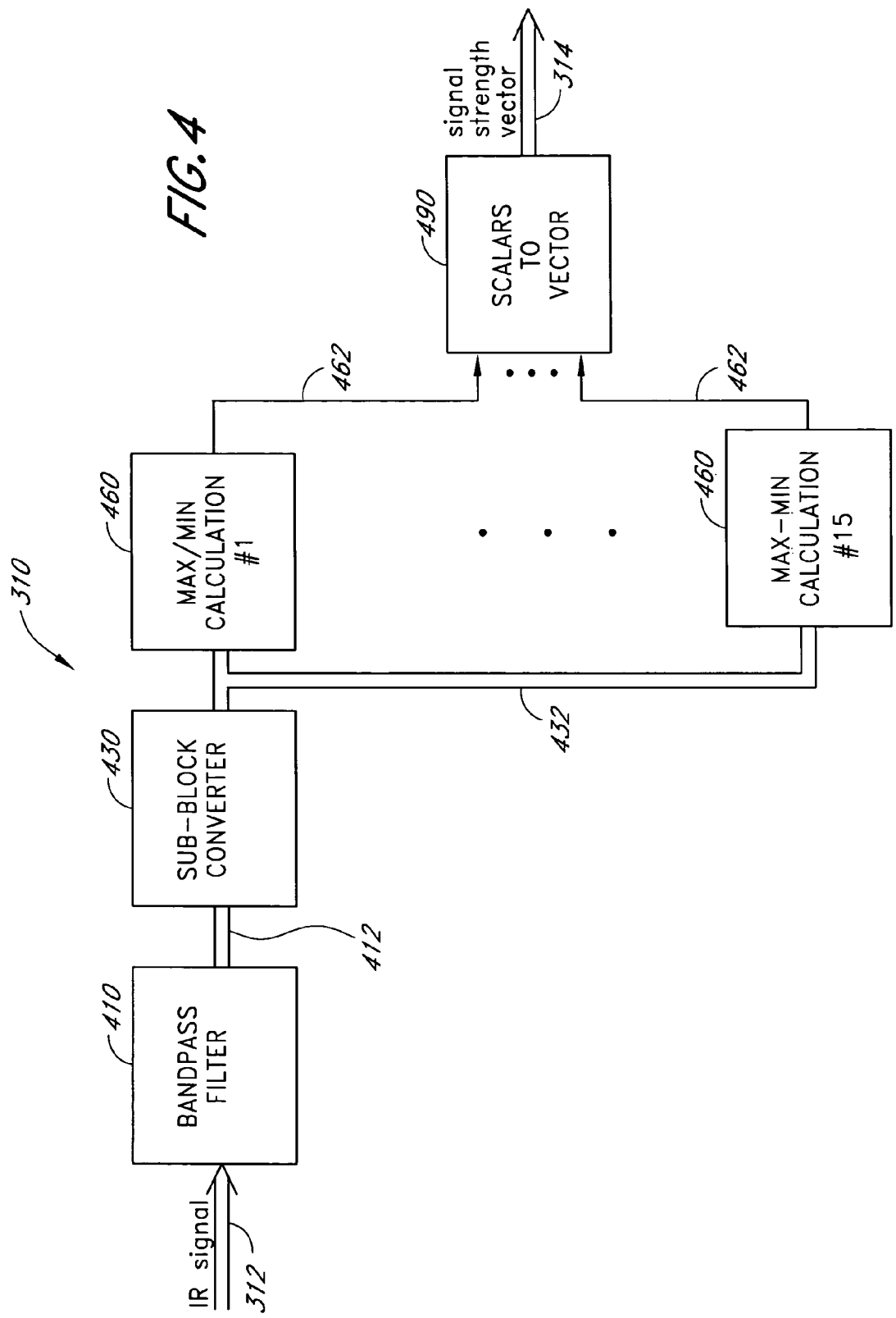

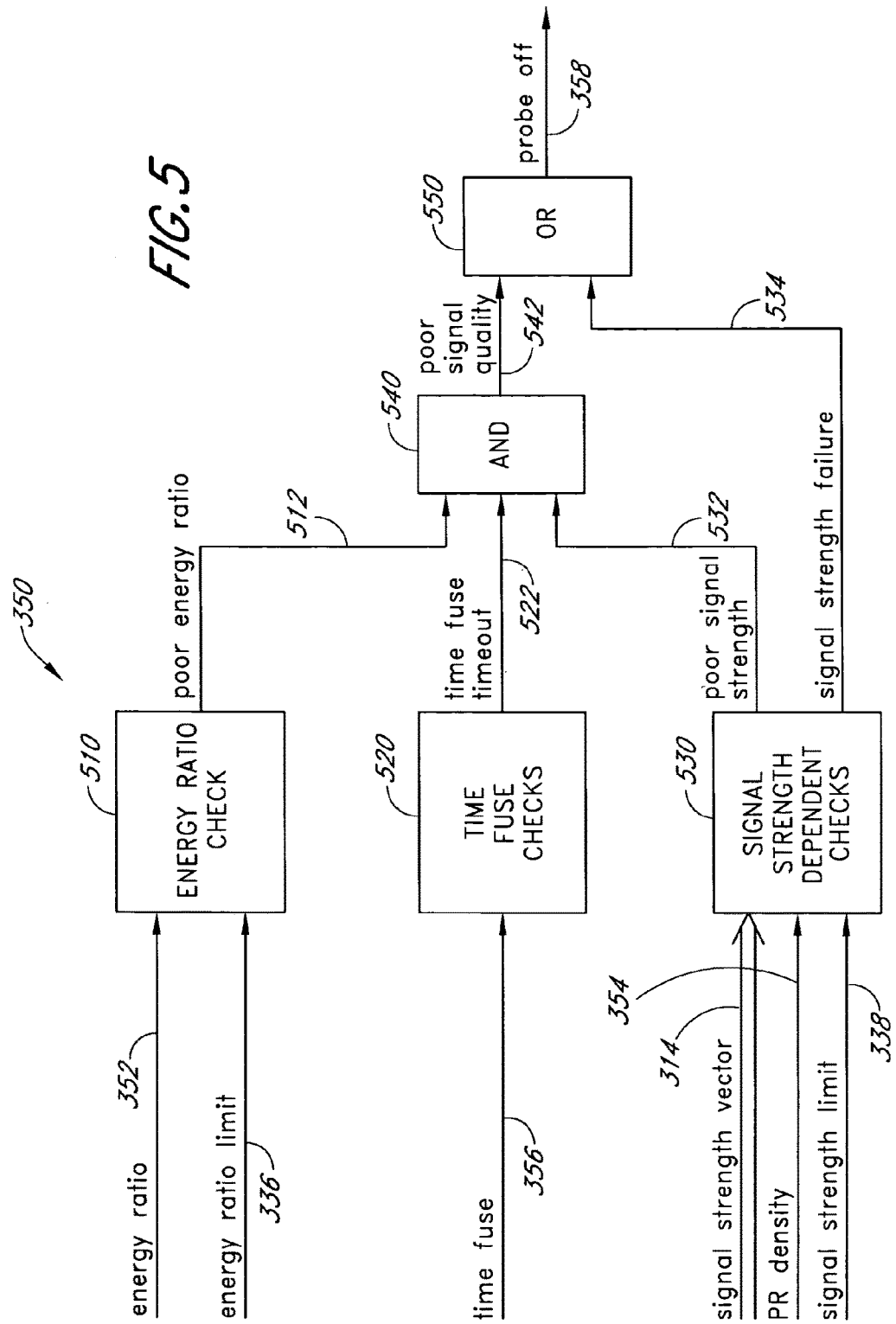

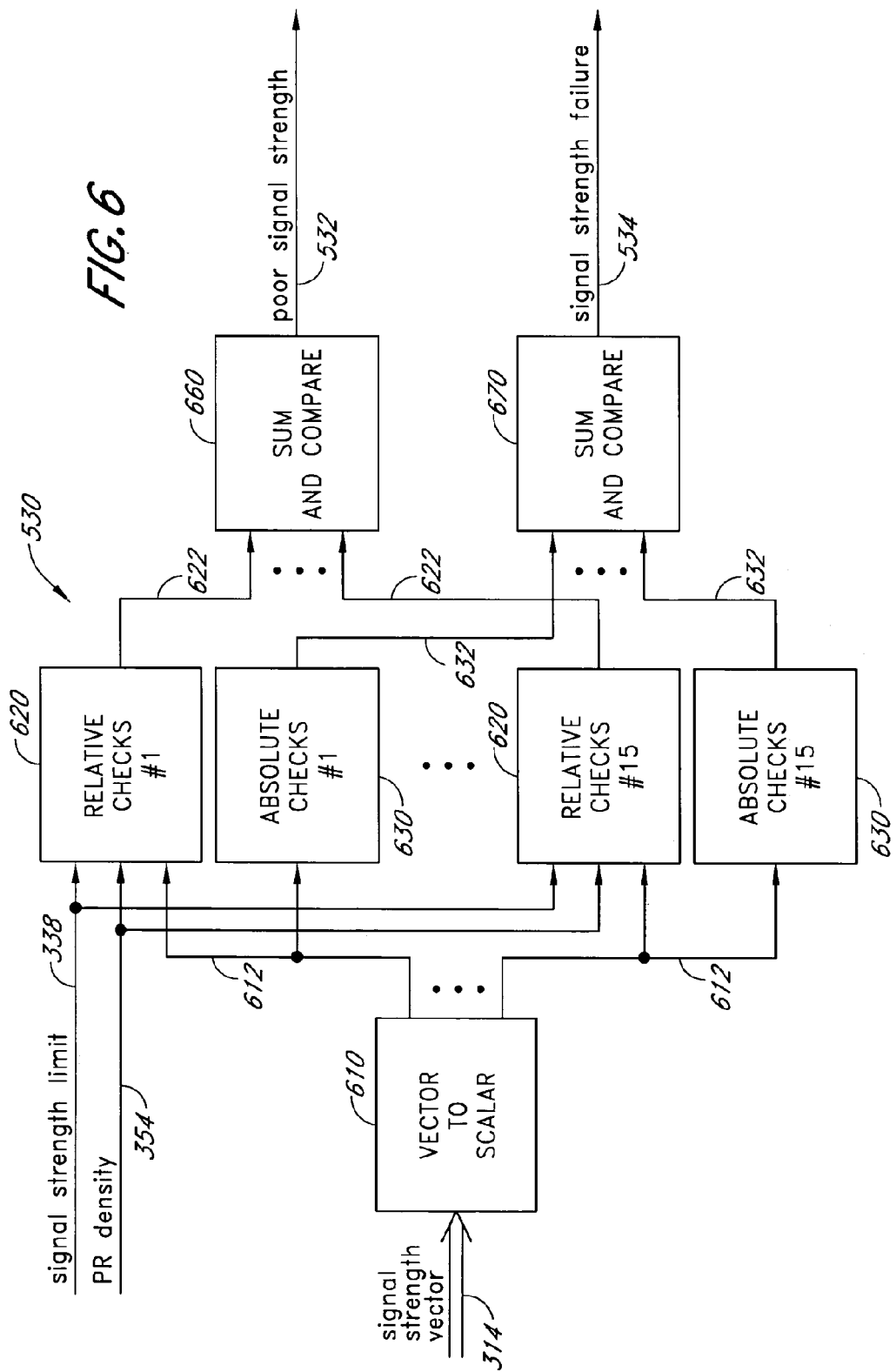

PULSE OXIMETER PROBE-OFF DETECTOR

REFERENCE TO RELATED APPLICATION

The present application claims priority benefit under 35 U.S.C. §120 to, and is a continuation of U.S. patent application Ser. No. 12/345,537, filed Dec. 29, 2008, entitled "Pulse Oximeter Probe-Off Detector," now U.S. Pat. No. 8,532,728, which is a continuation of U.S. patent application Ser. No. 10/721,607, filed Nov. 25, 2003, entitled "Pulse Oximeter Probe-Off Detector," now U.S. Pat. No. 7,471,969, which is a continuation of U.S. application Ser. No. 10/027,574, filed Dec. 19, 2001, entitled "Pulse Oximeter Probe-Off Detector," now U.S. Pat. No. 6,654,624, which is a continuation of U.S. application Ser. No. 09/531,820, filed Mar. 21, 2000, entitled "Pulse Oximeter Probe-Off Detector," now U.S. Pat. No. 6,360,114, which claims a priority benefit under 35 U.S.C. §119(e) from U.S. Provisional No. 60/126,148, filed Mar. 25, 1999, entitled "Improved Pulse Oximeter Probe-Off Detector." The present application incorporates by reference all of the foregoing.

BACKGROUND OF THE INVENTION

Description of the Related Art

Oximetry is the measurement of the oxygen status of blood. Early detection of low blood oxygen is critical in the medical field, for example in critical care and surgical applications, because an insufficient supply of oxygen can result in brain damage and death in a matter of minutes. Pulse oximetry is a widely accepted noninvasive procedure for measuring the oxygen saturation level of arterial blood, an indicator of oxygen supply. A pulse oximetry system consists of a sensor attached to a patient, a monitor, and a cable connecting the sensor and monitor. Conventionally, a pulse oximetry sensor has both red and infrared (IR) light-emitting diode (LED) emitters and a photodiode detector. The sensor is typically attached to a patient's finger or toe, or a very young patient's foot. For a finger, the sensor is configured so that the emitters project light through the fingernail and into the blood vessels and capillaries underneath. The photodiode is positioned at the fingertip opposite the fingernail so as to detect the LED transmitted light as it emerges from the finger tissues.

The pulse oximetry monitor (pulse oximeter) determines oxygen saturation by computing the differential absorption by arterial blood of the two wavelengths emitted by the sensor. The pulse oximeter alternately activates the sensor LED emitters and reads the resulting current generated by the photodiode detector. This current is proportional to the intensity of the detected light. The pulse oximeter calculates a ratio of detected red and infrared intensities, and an arterial oxygen saturation value is empirically determined based on the ratio obtained. The pulse oximeter contains circuitry for controlling the sensor, processing the sensor signals and displaying the patient's oxygen saturation and pulse rate. A pulse oximeter is described in U.S. Pat. No. 5,632,272 assigned to the assignee of the present invention.

SUMMARY OF THE INVENTION

To compute peripheral arterial oxygen saturation, denoted $Sp_aO_2$, pulse oximetry relies on the differential light absorption of oxygenated hemoglobin, $HbO_2$, and deoxygenated hemoglobin, Hb, to compute their respective concentrations in the arterial blood. This differential absorption is measured at the red and infrared wavelengths of the sensor. In addition, pulse oximetry relies on the pulsatile nature of arterial blood to differentiate hemoglobin absorption from absorption of other constituents in the surrounding tissues. Light absorption between systole and diastole varies due to the blood volume change from the inflow and outflow of arterial blood at a peripheral tissue site. This tissue site might also comprise skin, muscle, bone, venous blood, fat, pigment, etc., each of which absorbs light. It is assumed that the background absorption due to these surrounding tissues is invariant and can be ignored. Accordingly, blood oxygen saturation measurements are based upon a ratio of the time-varying or AC portion of the detected red and infrared signals with respect to the time-invariant or DC portion. This AC/DC ratio normalizes the signals and accounts for variations in light pathlengths through the measured tissue.

FIG. 1 illustrates the typical operating characteristics of a pulse oximeter. During a calibration phase, the pulse oximeter input gain is adjusted higher to accommodate opaque skin and lower to accommodate translucent skin at the sensor site. Variations in blood perfusion at the sensor site result in variations in input signal strength. The graph 100 shows acceptable input sensitivity as a function of gain. The y-axis 110 represents the signal strength (SS), which is the ratio of the peak-to-peak AC signal to the DC signal, expressed as a percentage. The x-axis 120 represents the gain, which is shown with decreasing values along the x-axis. The graph 100 has an unshaded region 130 representing the acceptable operating range of the pulse oximeter and a shaded region 140 representing conditions outside that operating range, which, when detected, will result in a pulse oximeter "probe off" alarm. The operating region 130 has a floor 150 at relatively low gains, representing the highest sensitivity to patients with low perfusion. Because input noise increases with gain, the operating region also has a corner point 160 below which input sensitivity is noise limited and falls off with increasing gain, i.e. increasing opacity.

A pulse oximeter with the operating characteristics shown in FIG. 1 may fail to detect a probe off condition. This problem occurs when the sensor becomes partially or completely dislodged from the patient, but continues to detect an AC signal within the operating region of the pulse oximeter. Probe off errors are serious because the pulse oximeter may display a normal saturation when, in fact, the probe is not properly attached to the patient, potentially leading to missed desaturation events.

Failure to detect a probe off condition is the result of the sensor detector receiving light directly from the emitters without transmission through the patient's tissue. The pulse oximeter is particularly vulnerable to probe off errors when operating at its highest sensitivity, where even small induced variations in light directly detected from the emitters have sufficient signal strength to be processed as a physiological signal. In a probe off condition, a detector AC signal can be induced by slight changes in the direct light path between the emitters and detector. For example, small amounts of patient motion, such as chest movement from breathing, can induce a probe off AC signal. As another example, "creep" in the sensor configuration, such as a folded sensor gradually returning to its original unfolded shape after becoming dislodged can also induce a probe off AC signal. Further restricting the operating region 130 shown in FIG. 1 can reduce probe off errors. Such restrictions, however, would also severely limit the ability of the pulse oximeter to make saturation measurements on patients with poor perfusion.

The present invention is a monitor-based improvement to detecting the probe off condition described above. Ofcourse, other methods of detecting the probe-off condition could be combined with the present improvement. In particular, an intelligent, rule-based processor uses signal quality measurements to limit the operating region of the pulse oximeter without significant negative impact on low perfusion performance. These signal-quality operating limits are superimposed on those of FIG. 1 to improve probe off detection. In this manner, the pulse oximeter can reject AC signals that have sufficient signal strength to fall within the operating region 130 of FIG. 1, but that are unlikely to be a plethysmograph signal. One signal quality measurement that is used is pulse rate density, which is the percentage of time detected pulses satisfy a physiologically acceptable model. Another signal quality measurement is energy ratio, which is the percentage of signal energy that occurs at the pulse rate and its harmonics. The operating region of the pulse oximeter is then defined in terms of signal strength versus gain, signal strength versus PR density and energy ratio versus predefined energy ratio limits.

In one embodiment of the present invention, a probe-off detector has a signal input, a signal quality input and a probe-off output. The signal quality input is dependent on a comparison between a sensor output and a physiological signal model. The probe-off output provides an indication that the sensor may not be properly attached to a tissue site. The detector includes a signal strength calculator, a stored relationship between signal strength and signal quality, and probe-off logic. The signal strength calculator has an input in communications with the sensor signal and provides a signal strength output that is dependent on the time-varying component of the sensor signal. The stored relationship defines an acceptable operating region for the sensor. The probe-off logic includes the signal strength and the signal quality as inputs and provides the probe-off output based on a comparison of the signal strength and the signal quality with the stored relationship.

In one embodiment, the probe-off logic includes a comparator, and in another embodiment, the probe-off logic includes an energy ratio check. In yet another embodiment, the probe-off logic includes a time check that indicates that no acceptable pulses have occurred for a sufficient time period.

In another embodiment of the present invention, a pulse oximetry sensor signal is processed to determine if it is properly attached to a tissue site. The method includes determining a signal strength limit that is dependent on signal quality, calculating a signal strength value from the sensor signal, calculating a signal quality value of the sensor signal and indicating a probe-off condition when the signal strength value is below the signal strength limit for the signal quality value.

BRIEF DESCRIPTION OF THE DRAWINGS

FIGS. 2A and 2B are graphs illustrating additional minimum signal strength operating limits for a pulse oximeter, based on signal quality according to the present invention;

FIG. 2A is a graph of signal quality operating limits for a pulse oximeter in normal input sensitivity mode;

FIG. 2B is a graph of signal quality operating limits for a pulse oximeter in high input sensitivity mode;

FIG. 4 is a detailed block diagram of the signal strength calculator portion of FIG. 3;

FIG. 5 is a detailed block diagram of the probe off logic portion of FIG. 3; and FIG. 6 is a detailed block diagram of the signal strength dependent checks portion of FIG. 5.

DETAILED DESCRIPTION OF THE PREFERRED EMBODIMENT

Figure 1:
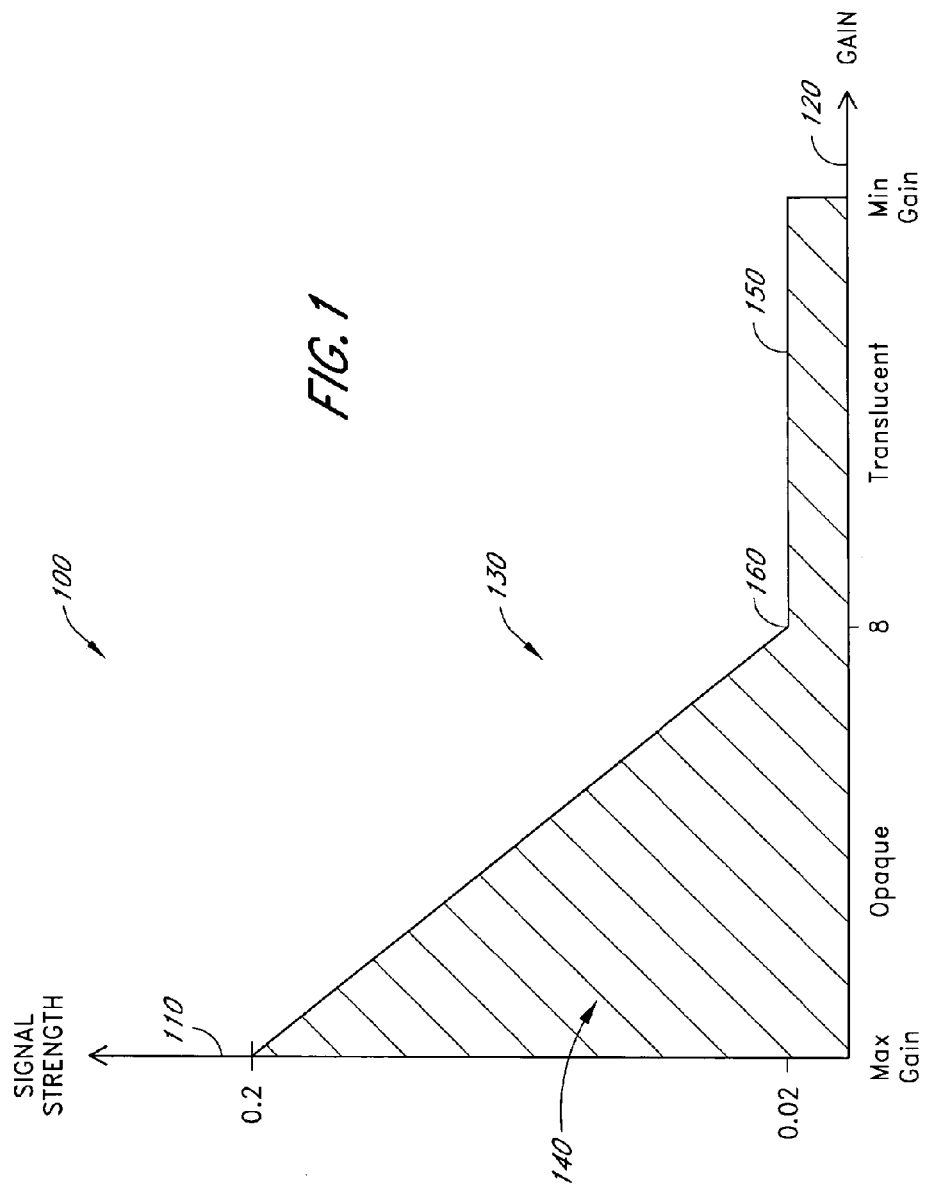
FIG. 1 is a graph illustrating minimum signal strength operating limits for a pulse oximeter.
Figure 2B:
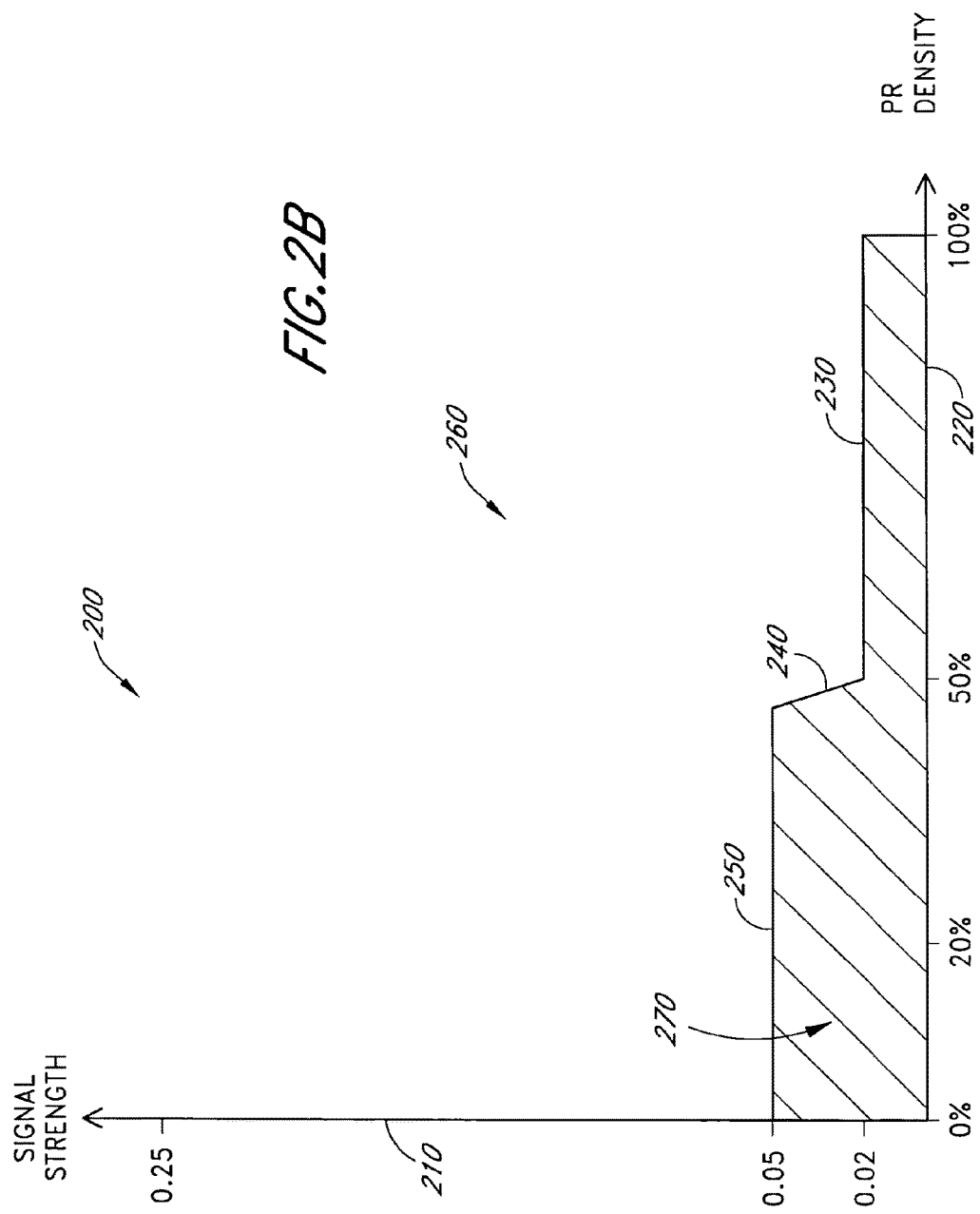

FIGS. 2A and 2B illustrate how the operating range of a pulse oximeter is modified based on pulse rate density according to one embodiment of the present invention. Calculation of PR density is disclosed in U.S. Provisional Patent Application No. 60/114,127 filed Dec. 30, 1998, and in U.S. patent application Ser. No. 09/471,510, filed Dec. 23, 1999, entitled "Plethysmograph Pulse Recognition Processor," which are assigned to the assignee of the current application and incorporated by reference herein. The processor described therein has a candidate pulse portion that determines a plurality of potential pulses within the input IR waveform. A physiological model portion of the processor then determines the physiologically acceptable ones of these potential pulses. The processor provides statistics regarding the acceptable pulses. One statistic is pulse density, which is the ratio of the period of acceptable pulses to the duration of a block or "snapshot" of the IR input waveform.

The physiological model portion of the processor has a series of components that discard potential pulses that do not compare to a physiologically acceptable pulse. The first component of the model portion extracts features of the potential pulses, including pulse starting point, pulse period, and pulse signal strength. These features are compared against various checks, including checks for pulses that have a period below a predetermined threshold, that are asymmetric, that have a descending trend that is generally slower that a subsequent ascending trend, that do not sufficiently comply with an empirical relationship between pulse rate and pulse signal strength, and that have a signal strength that differs from a short-term average signal strength by greater than a predetermined amount.

FIG. 2A shows a graph 200 of signal strength on the y-axis 210 versus PR density on the x-axis 220 for normal sensitivity. The operating region 260 is shown unshaded, and the probe off region 270 is shown shaded. A signal strength floor 230 of 0.02, below which a probe off condition exists for all values of PR density, determines one portion of the operating region 260. That is, no matter how many of the detected plethysmograph pulses are deemed physiologically acceptable, if the signal strength is less than 0.02, then the pulse oximeter indicates a probe off condition. A signal strength ceiling 250 of 0.25, above which the pulse oximeter is in a valid operating region for all values of PR density, determines another portion of the operating region 260. That is, signal quality is ignored if signal strength is above 0.25. Between the signal strength ceiling 250 and floor 230, acceptable signal strength is dependent on PR density. The slope of the boundary 240 defining this relationship is:

$$\text{slope}=-(0.25-0.02)/(0.5-0.2)=-0.23/0.3=-0.7667 \quad (1)$$

Thus, this boundary can be defined by the following equivalent equations:

$$SS=-0.7667 \cdot PR \text{ density}+0.4033 \quad (2)$$

$$PR \text{ density}=-1.3043 \cdot SS+0.5261 \quad (3)$$

FIG. 2B shows a graph 200 of signal strength on the y-axis 210 versus PR density on the x-axis 220 for high sensitivity. This graph is equivalent to that of FIG. 2A except that the signal strength ceiling 250 is set at 0.05. Thus, signal quality indicated by PR density is ignored as long as the signal strength is above 0.05.

Another signal quality measure, energy ratio, is also imposed on the operating region as an absolute limit. Energy ratio is the percentage of IR signal energy occurring at the pulse rate and associated harmonics compared to total IR energy. The energy ratio is computed by transforming each block of the IR signal into the frequency domain as is well known in the art. The energy ratio is computed by identifying each peak in the resulting spectrum. In one embodiment, the peaks occurring at the pulse rate and its harmonics are identified and summed. This value is divided by the sum of the magnitudes of all peaks and output as the energy ratio. Note that energy ratio computed in this manner is not a true energy calculation because the calculations are based on the peak magnitudes and not the squared magnitudes of the IR signal. In this embodiment, the minimum energy ratio must be 0.6 if the pulse rate is greater than or equal to 30 and 0.5 otherwise. That is, 60% (or 50% for low pulse rates) of the signal must be at the pulse rate frequency or its harmonics or the pulse oximeter will indicate a probe off condition. A method for calculating the pulse rate used in this calculation is disclosed in U.S. Pat. No. 6,002,952, filed Apr. 14, 1997, entitled "Improved Signal Processing Apparatus and Method," which is assigned to the assignee of the current application and incorporated by reference herein.

Figure 3:
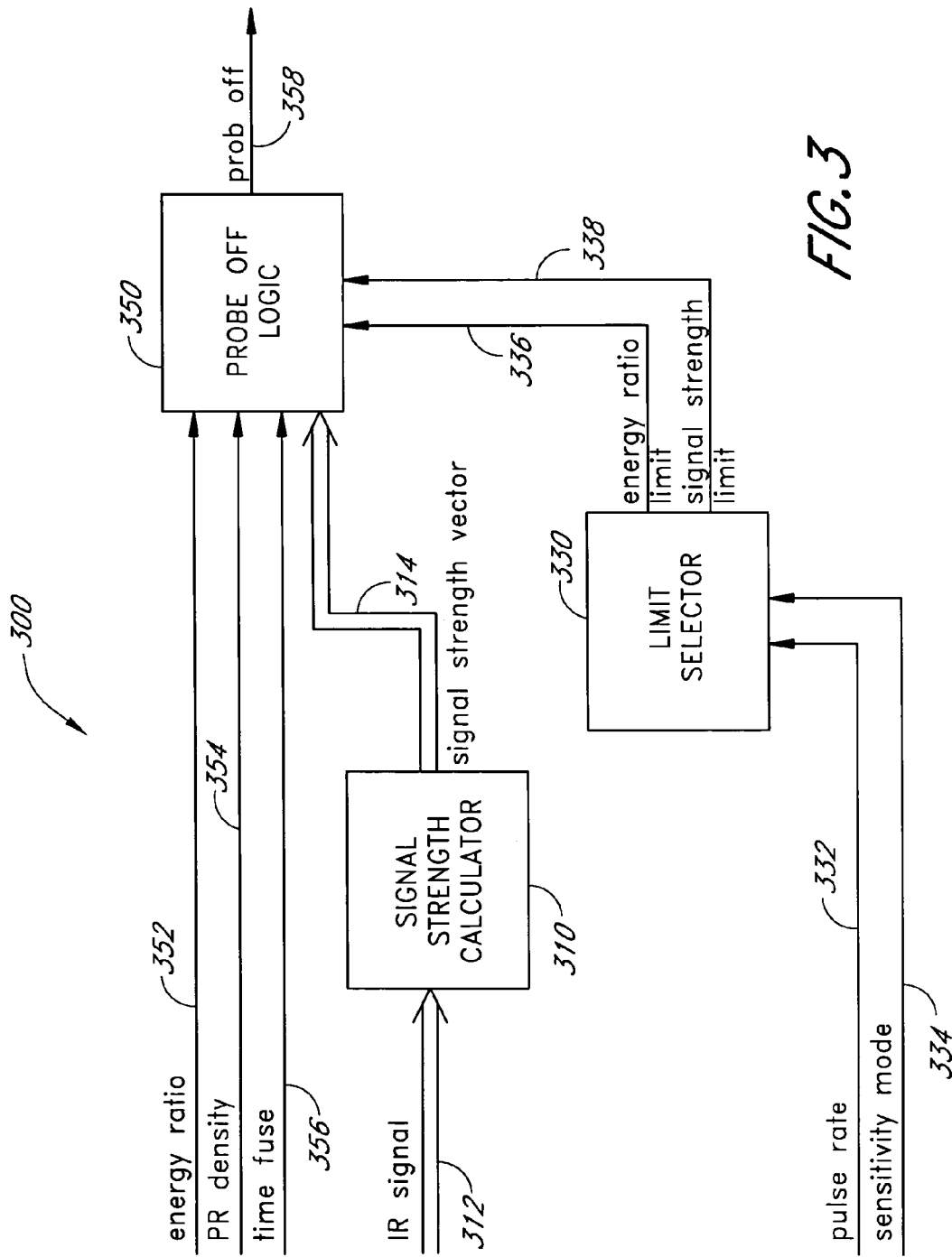
FIG. 3 is a top-level block diagram of a rule-based intelligent processor that provides the signal quality operating limits illustrated in FIGS. 2A-2B.

FIG. 3 is a block diagram illustrating one embodiment of the improved probe-off detector 300 according to the present invention. The detector has a signal strength calculator 310, a limit selector 330 and probe-off logic 350. The signal strength calculator 310 has an IR signal 312 input. This signal is the detected sensor signal after demultiplexing, amplification, filtering and digitization. In a particular embodiment, the IR signal is input to the signal strength calculator 310 at a 62.5 Hz sample rate and in overlapping "snapshots" or blocks of 390 samples, each offset from the previous block by 25 samples. The signal strength calculator 310 creates a signal strength vector output 314 consisting of a set of signal strength scalars for each of these input blocks, as described with respect to FIG. 4 below.

The limit selector 330 has pulse rate 332 and sensitivity mode 334 inputs. When the sensitivity mode input 334 has a value of 1, it indicates that the pulse oximeter is in a normal sensitivity mode, corresponding to FIG. 2A. A value of 0 indicates the pulse oximeter is in a high sensitivity mode, corresponding to FIG. 2B. The pulse oximeter operator selects the sensitivity mode. The limit selector 330 also has energy ratio limit 336 and signal strength limit 338 outputs, which are input to the probe off logic 350 as absolute minimums of energy ratio and signal strength below which a probe off condition may be indicated. The relationship between the pulse rate 332 and sensitivity mode 334 inputs and the energy ratio limit 336 and signal strength limit 338 outputs is specified below:

| INPUT STATE | SELECTED LIMIT |
|---|---|
| pulse rate ≥ 30 | minimum energy ratio = 0.6 |
| pulse rate < 30 | minimum energy ratio = 0.5 |
| sensitivity mode = 0 | minimum signal strength = 0.05 |
| sensitivity mode = 1 | minimum signal strength = 0.25 |

The probe off logic 350 has as inputs energy ratio 352, PR density 354 and signal strength vector 314. These inputs are compared to the energy ratio limit 336 and signal strength limit 338 outputs from the limit selector 330 to determine the operating region of the pulse oximeter. The probe off logic 350 also has a time fuse input 356. The time fuse 356 is a counter that indicates the number of IR waveform blocks containing no acceptable pulses. Acceptable pulses are determined as described for the calculation of PR density 354, above. The time fuse 356 input is −1 if there have been no acceptable pulses in a block since startup. The time fuse 356 is reset to 0 each time no acceptable pulses are detected for an input block. For each block where there are no acceptable pulses, the time fuse 356 is incremented by one. The time fuse enables the energy ratio limit and that portion of the signal strength limits above the floor 230 (FIGS. 2A-2B). This reduces the probability of probe off alarms for transient events. In a particular embodiment, the time fuse 356 is compared to the constants −1 and 5. That is, the energy ratio and signal strength limits are enabled if there have been no acceptable pulses since startup or for more than the previous 5 IR signal blocks.

The probe off logic 350 has a Boolean probe off output 358 that is set to 1 when the probe off logic 350 detects the pulse oximeter is operating outside permissible limits. Otherwise, the probe off output 358 is 0. The probe off output 358 can be used by the pulse oximeter to trigger a probe off alarm and error message to alert medical personnel to inspect and reattach the sensor or take other appropriate action. The probe off logic 350 is described in more detail below with respect to FIG. 5.

FIG. 4 shows further details of the signal strength calculator 310 (FIG. 3). Each 390 sample block of the IR signal 312 is initially filtered 410 to remove any trends in the IR signal 312 that could cause an error in the signal strength calculations. In a particular embodiment, the filter 410 is a bandpass FIR filter with cutoff frequencies of 50 Hz and 550 Hz and a 151 tap Kaiser window having a shape parameter of 3.906. As a result, 150 samples are lost from each 390 sample input block. Thus, the filtered IR output 412 consists of 240 sample blocks.

Each 240 sample block of the filtered IR output 412 is converted 430 into multiple overlapping sub-blocks. In a particular embodiment, the sub-blocks each consist of 100 samples, and each sub-block is offset by 10 samples from the previous sub-block. Thus, the sub-block converter 430 creates 15 sub-block outputs 432 for each 240 sample filtered IR block 412. For each sub-block, a max-min calculation 460 is performed. That is, the minimum sample magnitude in a particular sub-block is subtracted from the maximum sample magnitude in that sub-block. Each max-min output 462 is a single scalar representing the signal strength of a particular sub-block. A scalar-to-vector conversion 490 combines the max-min outputs 462 into a vector output 314 containing multiple signal strength values representing the signal strength of a particular block of the IR signal 312.

FIG. 5 provides further detail of the probe off logic 350 (FIG. 3). The probe off logic 350 has three functional checks that each provide a Boolean output. An energy ratio check 510 compares the energy ratio 352 against the energy ratio limit 336 provided by the limit selector 330 (FIG. 3), specified in the table above. The energy ratio check 510 sets the "poor energy ratio" output 512 if the energy ratio 352 is below the energy ratio limit 336.

A time fuse check 520 determines if the time fuse 356 indicates no acceptable pulses have occurred in the IR signal 312 (FIG. 3) for a sufficiently long time period. If so, a timeout output 522 is set. In a particular embodiment, the time fuse check 520 consists of comparators that determine if the time fuse 356 is −1 or greater than 5, indicating no acceptable pulses since startup or for a longer period than the past 5 blocks of IR signal 312.

The signal strength dependent checks 530 determine if the pulse oximeter is within the operating limits described above with respect to FIGS. 2A and 2B. If the signal strength, as determined by the signal strength vector 314, is below the floor 230 (FIGS. 2A-B), then the signal strength failure output 534 is set. If the signal strength is above the floor 230 (FIGS. 2A-B) but otherwise outside the operating region, i.e. within the shaded region 270 (FIGS. 2A-B) above the floor 230 (FIGS. 2A-2B), then the "poor signal strength" output 532 is set.

A logical AND function 540 sets a "poor signal quality" output 542 if the poor energy ratio 512, poor signal strength 532 and timeout 522 outputs are set. A logical OR function 550 sets the probe off output 358 if the poor signal quality 542 or the signal strength failure 534 outputs are set.

FIG. 6 shows a particular embodiment of the signal strength dependent checks 530 (FIG. 5). The signal strength vector 314 is converted 610 into the 15 individual signal strength scalars 612. Relative checks 620 and absolute checks 630 are performed on each of the 15 scalars 612. Each relative check 620 determines if signal strength is within the signal strength limit 338 relative to PR density 354. That is, each relative check output 622 is set according to the following, see Eq. 3 above:

| INPUT STATE | RESULT |
|---|---|
| SS ≥ SS limit | output = 0 |
| PR density > −1.3043 · SS + 0.5261 | output = 0 |
| (SS < SS limit) AND PR density < −1.3043 · SS + 0.5261 | output = 1 |

Each absolute check 630 determines if the signal strength is above the absolute minimum floor 230 (FIGS. 2A-2B). That is, each absolute check output 632 is set according to the following:

| INPUT STATE | RESULT |
|---|---|
| SS ≥ 0.02 | output = 0 |
| SS < 0.02 | output = 1 |

The 15 relative check outputs 622 are processed by a sum and compare 660, which performs an arithmetic sum of these outputs 622. If the sum is equal or greater than 5, the poor signal strength output 532 is set. That is, poor signal strength is indicated if at least ⅓ of the scalars in the signal strength vector 314 fail their relative checks 620. Likewise, the 15 absolute check outputs 632 are processed by a sum and compare 670, which performs an arithmetic sum of these outputs 632. If the sum is equal or greater than 5, the signal strength failure output 534 is set. That is, a signal strength failure is indicated if at least ⅓ of the scalars in the signal strength vector 314 fail the absolute checks 630.

This improvement to detecting pulse oximetry probe off conditions has been disclosed in detail in connection with various embodiments of the present invention. These embodiments are disclosed by way of examples only and are not to limit the scope of the present invention, which is defined by the claims that follow. One of ordinary skill in the art will appreciate many variations and modifications within the scope of this invention.

What is claimed is:

1. A patient monitor configured to obtain signals responsive to physiological parameters of a monitored patient and determine when a physiological sensor may not be properly attached to said monitored patient with respect to a measurement site, the patient monitor comprising:
   one or more processors configured to:
      receive a sensitivity mode setting;
      determine a signal strength limit based at least in part on the sensitivity mode setting;
      determine a signal strength of one or more signals indicative of one or more physiological parameters of a monitored patient, wherein the one or more signals comprise a plurality of pulses, each pulse comprising a plurality of pulse features;
      perform one or more checks on one or more pulse features to determine one or more physiologically acceptable pulses from the plurality of pulses, wherein the one or more features include at least one of pulse starting point, pulse period, or pulse signal strength;
      determine a pulse rate density indicative of a percentage of time physiologically acceptable pulses occur;
      determine a sensor not properly attached condition exists when the signal strength and the pulse rate density fall within a probe off region, wherein the probe off region is associated with the signal strength limit and wherein the probe off region corresponds to operating conditions outside an acceptable operating range; and
      indicate an alarm condition responsive to a determination that the sensor not properly attached condition exists.

2. The patient monitor of claim 1, wherein the signal strength of the one or more signals is based upon a ratio of a peak-to-peak AC signal to a DC signal.

3. The patient monitor of claim 1, wherein the signal strength limit is 0.05.

4. The patient monitor of claim 1, wherein the signal strength limit is 0.25.

5. The patient monitor of claim 1, wherein the signal strength limit is selectable by an operator.

6. The patient monitor of claim 1, wherein said signal strength limit is determined from a pulse rate of the monitored patient.

7. The patient monitor of claim 1, wherein the pulse rate density is indicative of a percentage of time a detected pulse rate of said one or more signals satisfies a physiologically acceptable model.

8. The patient monitor of claim 1, wherein physiologically acceptable pulses comprise pulses that are asymmetric.

9. The patient monitor of claim 1, wherein physiologically acceptable pulses comprise pulses that have a descending trend that is slower than a subsequent ascending trend.

10. The patient monitor of claim 1, wherein physiologically acceptable pulses comprise pulses having a signal strength that differs from a short-term average signal strength by greater than a predetermined amount.

11. The patient monitor of claim 1, wherein the one or more checks comprises at least one of a check for pulses that have a period below a predetermined threshold, a check for pulses that are asymmetric, a check for pulses that have a descending trend that is slower that a subsequent ascending trend, a check for pulses that do not comply with an empirical relationship between pulse rate and pulse signal strength, or a check for pulses that have a signal strength that differs from a short-term average signal strength by greater than a predetermined amount.

12. In a patient monitor configured to obtain signals responsive to physiological parameters of a monitored patient, a method for determining when a physiological sensor may not be properly attached to said monitored patient with respect to a measurement site, the method comprising:

receiving one or more setting signals indicative of one or more selectable settings;

determining a signal strength limit from the one or more setting signals;

determining a signal strength of one or more sensor signals indicative of one or more physiological parameters of a monitored patient, wherein the one or more signals comprise a plurality of pulses;

performing one or more checks on one or more pulse features to determine one or more physiologically acceptable pulses from the plurality of pulses, wherein the one or more features include at least one of pulse starting point, pulse period, or pulse signal strength;

determining a pulse rate density indicative of a percentage of time physiologically acceptable pulses occur;

determining a sensor not properly attached condition exists when the signal strength and the pulse rate density fall within a probe off region, wherein the probe off region is associated with the signal strength limit and wherein the probe off region corresponds to operating conditions outside an acceptable operating range; and indicating an alarm condition responsive to a determination that the sensor not properly attached condition exists.

13. The method of claim 12, wherein the determining a signal strength of the one or more sensor signals is based upon a ratio of a peak-to-peak AC signal to a DC signal.

14. The method of claim 12, wherein the signal strength limit is 0.05.

15. The method of claim 12, wherein the signal strength limit is 0.25.

16. The method of claim 12, wherein the signal strength limit is selectable by an operator.

17. The method of claim 12, wherein said signal strength limit is determined based on a pulse rate of the monitored patient.

18. The method of claim 12, wherein the pulse rate density is indicative of a percentage of time a detected pulse rate of said one or more sensor signals satisfies a physiologically acceptable model.

19. The method of claim 12, further comprising triggering, in response to a determination that a sensor not properly attached condition exists, an alarm configured to indicate a probe-off condition.

20. The method of claim 12, wherein physiologically acceptable pulses comprise pulses that are asymmetric.

21. The method of claim 12, wherein physiologically acceptable pulses comprise pulses that have a descending trend that is slower than a subsequent ascending trend.

22. The method of claim 12, wherein physiologically acceptable pulses comprise pulses having a signal strength that differs from a short-term average signal strength by greater than a predetermined amount.

23. The method of claim 12, wherein the one or more checks comprises at least one of a check for pulses that have a period below a predetermined threshold, a check for pulses that are asymmetric, a check for pulses that have a descending trend that is slower that a subsequent ascending trend, a check for pulses that do not comply with an empirical relationship between pulse rate and pulse signal strength, or a check for pulses that have a signal strength that differs from a short-term average signal strength by greater than a predetermined amount.

* * * * *